(12) United States Patent
Cahan et al.

(10) Patent No.: US 10,745,586 B2
(45) Date of Patent: Aug. 18, 2020

(54) FLUORINATED NETWORKS FOR ANTI-FOULING SURFACES

(71) Applicants: International Business Machines Corporation, Armonk, NY (US); Agency for Science, Technology and Research, Singapore (SG)

(72) Inventors: Amos Cahan, Netaim (IL); Xin Ding, Singapore (SG); Mareva B. Fevre, Oakland, CA (US); James L. Hedrick, Pleasanton, CA (US); Zhen Chang Liang, Singapore (SG); Nathaniel H. Park, San Jose, CA (US); Theodore G. van Kessel, Millbrook, NY (US); Rudy J. Wojtecki, San Jose, CA (US); Yi Yan Yang, Singapore (SG)

(73) Assignees: INTERNATIONAL BUSINESS MACHINES CORPORATION, Armonk, NY (US); AGENCY FOR SCIENCE, TECHNOLOGY, Singapore (SG)

( * ) Notice: Subject to any disclaimer, the term of this patent is extended or adjusted under 35 U.S.C. 154(b) by 34 days.

(21) Appl. No.: 15/671,639

(22) Filed: Aug. 8, 2017

(65) Prior Publication Data
US 2019/0048226 A1 Feb. 14, 2019

(51) Int. Cl.
*C09D 181/04* (2006.01)
*A61L 31/10* (2006.01)
(Continued)

(52) U.S. Cl.
CPC ............ *C09D 181/04* (2013.01); *A01N 33/08* (2013.01); *A61L 27/34* (2013.01); *A61L 27/54* (2013.01);
(Continued)

(58) Field of Classification Search
CPC ....... G01Q 80/00; C08G 75/14; C09D 181/04
See application file for complete search history.

(56) References Cited

U.S. PATENT DOCUMENTS 3,697,402 A 10/1972 Kehr et al.
4,565,740 A 1/1986 Golander et al.
(Continued)

FOREIGN PATENT DOCUMENTS

CA 2588832 A1 5/2006
EP 0346058 A1 12/1989
(Continued)

OTHER PUBLICATIONS

A. J. Domb, I. Yudovin-Farber, J. Golenser, N. Beyth, E. I. Weiss, QuaternaryAmmonium Polyethyleneimine: Antibacterial Activity. J. Nanomater. 2010, DOI 10.1155/2010/826343,12 pages.
(Continued)

*Primary Examiner* — Dah-Wei D. Yuan
*Assistant Examiner* — Andrew J Bowman
(74) *Attorney, Agent, or Firm* — Cantor Colburn LLP; Vazken Alexanian

(57) ABSTRACT

According to one or more embodiments, a method of making an antifouling coating includes forming a polythioaminal polymer by reacting a fluorinated primary amine with an aldehyde to form an intermediate imine, and then reacting the intermediate imine with a dithiol. The method further includes depositing the polythioaminal on a substrate, and increasing a temperature of the polythioaminal deposited on the substrate to crosslink the polythioaminal and increase a contact angle of the substrate with crosslinked polythioaminal.

20 Claims, 5 Drawing Sheets

(51) Int. Cl.

| | | |
|---|---|---|
| *A61L 31/16* | (2006.01) | |
| *C09D 5/14* | (2006.01) | |
| *A01N 33/08* | (2006.01) | |
| *B05D 1/02* | (2006.01) | |
| *A61L 27/54* | (2006.01) | |
| *A61L 29/08* | (2006.01) | |
| *A61L 29/16* | (2006.01) | |
| *C09D 5/16* | (2006.01) | |
| *A61L 27/34* | (2006.01) | |
| *B05D 5/08* | (2006.01) | |

(52) U.S. Cl.
CPC ............ *A61L 29/085* (2013.01); *A61L 29/16* (2013.01); *A61L 31/10* (2013.01); *A61L 31/16* (2013.01); *B05D 1/02* (2013.01); *C09D 5/14* (2013.01); *C09D 5/1662* (2013.01); *A61L 2300/404* (2013.01); *A61L 2300/406* (2013.01); *A61L 2420/02* (2013.01); *B05D 5/083* (2013.01)

(56) References Cited

U.S. PATENT DOCUMENTS

| | | | |
|---|---|---|---|
| 5,213,898 | A | 5/1993 | Larm et al. |
| 8,337,792 | B2 | 12/2012 | Westlund et al. |
| 8,895,354 | B2 | 11/2014 | Kugler et al. |
| 9,018,172 | B2 | 4/2015 | Pentelute et al. |
| 9,109,140 | B2 | 5/2015 | Dooley |
| 9,381,276 | B1 | 7/2016 | Joseph et al. |
| 9,399,044 | B2 | 7/2016 | Cheng et al. |
| 10,006,936 | B2 * | 6/2018 | Boday .................... C08G 16/02 |
| 10,563,069 | B2 | 2/2020 | Cahan et al. |
| 2003/0194504 | A1 | 10/2003 | Bilyk et al. |
| 2011/0086172 | A1 | 4/2011 | Snow |
| 2011/0171279 | A1 | 7/2011 | Chisholm et al. |
| 2012/0058355 | A1 | 3/2012 | Lee et al. |
| 2013/0302873 | A1 | 11/2013 | Singh et al. |
| 2014/0004170 | A1 | 1/2014 | Kronen et al. |
| 2014/0010983 | A1 * | 1/2014 | Gorodisher ............ C08L 63/00 428/41.8 |
| 2014/0113871 | A1 | 4/2014 | Pentelute et al. |
| 2014/0242866 | A1 | 8/2014 | Locklin |
| 2014/0319044 | A1 | 10/2014 | Giannellis et al. |
| 2014/0342954 | A1 | 11/2014 | Ingber et al. |
| 2014/0369953 | A1 | 12/2014 | Purschwitz et al. |
| 2015/0093425 | A1 | 4/2015 | Moore |
| 2015/0148903 | A1 | 5/2015 | Robeson et al. |
| 2015/0249137 | A1 | 9/2015 | Katsuhara et al. |
| 2015/0328378 | A1 | 11/2015 | Schaer et al. |
| 2015/0369771 | A1 | 12/2015 | Richardson-Burns et al. |
| 2016/0002103 | A1 | 1/2016 | Wang et al. |
| 2016/0165926 | A1 | 6/2016 | Medoff |
| 2016/0200967 | A1 | 7/2016 | Mahoney et al. |
| 2016/0228574 | A1 | 8/2016 | Farokhzad et al. |
| 2016/0237305 | A1 | 8/2016 | Advincula et al. |
| 2018/0163020 | A1 | 6/2018 | Zong et al. |
| 2018/0282556 | A1 | 10/2018 | Cahan et al. |
| 2018/0303979 | A1 | 10/2018 | Cahan et al. |
| 2019/0048208 | A1 | 2/2019 | Cahan et al. |
| 2019/0048226 | A1 | 2/2019 | Cahan et al. |
| 2019/0144610 | A1 | 5/2019 | Moser et al. |
| 2019/0313642 | A1 | 10/2019 | Lienkamp et al. |
| 2020/0071543 | A1 | 3/2020 | Cahan |

FOREIGN PATENT DOCUMENTS

| | | |
|---|---|---|
| EP | 2289971 A1 | 3/2011 |
| EP | 2350116 A1 | 8/2011 |
| WO | 2008106194 A1 | 9/2008 |
| WO | 2010038040 A1 | 4/2010 |
| WO | 2014120095 A1 | 8/2014 |
| WO | 2014152423 A1 | 9/2014 |
| WO | 2018198003 A1 | 11/2018 |

OTHER PUBLICATIONS

A. J. McBain et al., "Microbial Characterization of Biofilms in Domestic Drains and the Establishment of Stable Biofilm Microcosms", Applied and Environmental Microbiology, 69(1), Jan. 2003, pp. 177-185.

B. A. Lander et al., "Extracytoplasmic Stress Responses Induced by Antimicrobial Cationic Polyethylenimines", Current Microbiology, 65(5), 2012, pp. 488-492.

B. Schachter, "Slimy business—the biotechnology of biofilms", Nature Biotechnology, 21(4), Apr. 2003, pp. 361-365.

Behlau, I., Mukherjee, K., Todani, A. et al. (2011). Biocompatibility and biofilm inhibition of N, N-hexyl, methyl-polyethylenimine bonded to Boston Keratoprosthesis materials. Biomaterials, 32(34), pp. 8783-8796.

C. G. Kumar et al., "Significance of microbial biofilms in food industry: a review", International Journal of Food Microbiology, 42(1), 1998, pp. 9-27.

C. Tedjo, "Bacteria-surface interaction in the presence of proteins and surface attached poly(ethylene glycol) methacrylate chains", Journal of Biomedical Materials Research Part A, 82(2), 2007, pp. 479-491.

Z. X. Voo et al., "Antimicrobial coatings against biofilm formation: the unexpected balance between antifouling and bactericidal behavior", Polymer Chemistry, 7(3), 2016, pp. 656-668.

C. Wiegand et al., "Poly(ethyleneimines) in dermal applications: Biocompatibility and antimicrobial effects", International Journal of Pharmaceutics, 456(1), 2013, pp. 165-174.

D. Davies, "Understanding biofilm resistance to antibacterial agents", Nature Reviews Drug discovery, 2(2), 2003, pp. 114-122.

Y. Nakagawa et al., "Synthesis of highly refractive poly(phenylene thioether)s containing a binaphthyl or diphenylfluorene unit", Polymer Chemistry, 3, 2012, pp. 2531-2536.

D. Han et al., "Synthesis of fluorinated monomer and formation of hydrophobic surface therefrom," RSC Adv., 5, 2015, pp. 22847-22855.

De Prijck, K., De Smet, N., Coenye, T. et al. (2010). Prevention of Candida albicans biofilm formation by covalently bound dimethylaminoethylmethacrylate and polyethylenimine. Mycopathologia, 170(4), 213-221.

Faris, A. H., Rahim, A. A., Ibrahim, M. N. M. et al. (2016). Combination of lignin polyol-tannin adhesives and polyethylenimine for the preparation of green water-resistant adhesives. Journal of Applied Polymer Science, 133(20), 6 pages.

George, S. (2015). Nanomaterial Properties: Implications for Safe Medical Applications of Nanotechnology. Nanotechnology in Endodontics, 45-69.

H. Khalil et al., "Synergy between Polyethylenimine and Different Families of Antibiotics against a Resistant Clinical Isolate of Pseudomonas aeruginosa", Antimicrobial Agents and Chemotherapy, 52(5), May 2008, pp. 1635-1641.

I. Banerjee et al., "Antifouling Coatings: Recent Developments in the Design of Surfaces That Prevent Fouling by Proteins, Bacteria, and Marine Organisms", Advanced Materials, 23(6), 2011, pp. 690-718.

Ishikawa "Superbases for Organic Synthesis: Guanidines, Amidines, Phosphazenes and Related Organocatalysts," Wiley Publication, Mar. 2009, 340 pages.

J. A. Shapiro, "Thinking about bacterial populations as multicellular organisms", Annual Reviews in Microbiology, 52 (1), 1998, pp. 81-104.

J. Dong et al., "SuFEx-Based Synthesis of Polysulfates", Angewandte Chemie International Edition, 53 (36), 2014, pp. 9466-9470.

J. Hasan et al., "Antibacterial surfaces: the quest for a new generation of biomaterials", Trends in Biotechnology, 31(5), May 2013, pp. 295-304.

J. M. Garcia et al., "Meisenheimer Complex Inspired Catalyst- and Solvent-Free Synthesis of Noncyclic Poly(aryl ether sulfone)s", Macromolecules, 47(23), 2014, pp. 8131-8136.

J. S. Price et al., "Controlled release of antibiotics from coated orthopedic implants", Journal of Biomedical Materials Research Part A, 30(3), 1996, pp. 281-286.

(56) References Cited

OTHER PUBLICATIONS

J. Yatvin et al., "Durable defense: robust and varied attachment of non-leaching poly"-onium" bactericidal coatings to reactive and inert surfaces", Chemical Communications, 50(67), 2014, pp. 9433-9442.

Khan, S., Ul-Islam, M., Ullah, M. W. et al. (2015). Synthesis and characterization of a novel bacterial cellulose-poly(3,4-ethylenedioxythiophene)-poly (styrene sulfonate) composite for use in biomedical applications. Cellulose, 22(4), 2141-2148.

Kondoh, A., Yorimitsu, H., & Oshima, K. (2006). Nucleophilic aromatic substitution reaction of nitroarenes with alkyl-or arylthio groups in dimethyl sulfoxide by means of cesium carbonate. Tetrahedron, 62(10), 2357-2360.

L. Hall-Stoodley et al., "Bacterial biofilms: from the natural environment to infectious diseases", Nature Reviews Microbiology, 2(2), Feb. 2004, pp. 95-108.

M. Charnley et al., "Designed polymer structures with antifouling-antimicrobial properties", Reactive & Functional Polymers, 71(3), 2011, pp. 329-334.

M. E. Samberg et al., "Silver Nanoparticles in Biomedical Applications", Nanotoxicology: Progress toward Nanomedicine, CRC Press, 2014, pp. 405-421.

M. M. Azevedo et al., "Polyethyleneimine and polyethyleneimine-based nanoparticles: novel bacterial and yeast biofilm inhibitors", Journal of Medical Microbiology, 63(9), 2014, pp. 1167-1173.

N. Blanchemain et al., "Vascular prostheses with controlled release of antibiotics: Part 1: Surface modification with cyclodextrins of PET prostheses", Biomolecular Engineering, 24(1), 2007, pp. 149-153.

N. Sahiner et al., "The synthesis of desired functional groups on PEI microgel particles for biomedical and environmental applications", Applied Surface Science, 354, 2015, pp. 380-387.

O'Shea, J. P., Solovyeva, V., Guo, X. et al. (2014). Sequence-controlled copolymers of 2, 3, 4, 5-pentafluorostyrene: mechanistic insight and application to organocatalysis. Polymer Chemistry, 5(3), pp. 698-701.

Peraro, L., Siegert, T. R., & Kritzer, J. A. (2016). Chapter Fourteen—Conformational Restriction of Peptides Using Dithiol Bis-Alkylation. Methods in Enzymology, 580, pp. 303-332.

Raad, I., Hachem, R., Zermeno, A. et al. (1996). Silver iontophoretic catheter: A prototype of a long-term antiinfective vascular access device. Journal of Infectious Diseases, 173(2), pp. 495-498.

S. A. Koplin et al., "Evaluation of the Antimicrobial Activity of Cationic Polyethylenimines on Dry Surfaces", Biotechnology Progress, 24(5), 2008, pp. 1160-1165.

S. Eckhardt et al., "Nanobio Silver: Its Interactions with Peptides and Bacteria, and Its Uses in Medicine", Chemical Reviews, 113(7), 2013, pp. 4708-4754.

S. Matsumura et al., "Synthesis and Properties of Novel Aromatic Poly(thioether-ketone)s as Sulfur-Containing High-Performance Polymers", Macromolecules, 34(9), 2001, pp. 2848-2853.

S. Q. Liu et al., "Antimicrobial and Antifouling Hydrogels Formed In Situ from Polycarbonate and Poly(ethylene glycol) via Michael Addition", Advanced Materials, 24(48), 2012, pp. 6484-6489.

S. Seesukphronrarak et al., "Synthesis of Fluorene-Based High Performance Polymers. I. Poly(arylene thioether)s with Excellent Solubility and High Refractive Index", Journal of Polymer Science Part A: Polymer Chemistry, 45(14), 2007, pp. 3073-3082.

Secinti, K. D., Ayten, M., Kahilogullari, G. et al. (2008). Antibacterial effects of electrically activated vertebral implants. Journal of Clinical Neuroscience, 15(4), pp. 434-439.

Stoodley, P., & Lappin-Scott, H. M. (1997). Influence of electric fields and pH on biofilm structure as related to the bioelectric effect. Antimicrobial agents and chemotherapy, 41(9), 1876-1879.

T. Higashihara et al., "Recent Progress in High Refractive Index Polymers", Macromolecules, 48(7), 2015, pp. 1915-1929.

W. Cheng et al., "Broad-Spectrum Antimicrobial/Antifouling Soft Material Coatings Using Poly(ethylenimine) as a Tailorable Scaffold", Biomacromolecules, 16(7), 2015, pp. 1967-1977.

Y. He et al., "Synthesis and Characterization of Amphiphilic Monodisperse Compounds and Poly(ethylene imine)s: Influence of Their Microstructures on the Antimicrobial Properties", Biomacromolecules, 13(3), 2012, pp. 612-623.

Y. Nakagawa et al. "Synthesis of Highly Refractive Poly(phenylene thioether) Derived from 2,4-Dichloro-6-alkylthio-1,3,5-triazines and Aromatic Dithiols", Macromolecules, 44(23), 2011, pp. 9180-9186.

Amos Cahan, et al.; "Prevention of Biofilm Formation"; U.S. Appl. No. 16/678,076, filed Nov. 8, 2019.

Amos Cahan, et al.; "Prevention of Biofilm Formation"; U.S. Appl. No. 16/678,315, filed Nov. 8, 2019.

Amos Cahan, et al.; "Tailorable Surface Topology for Antifouling Coatings"; U.S. Appl. No. 16/675,754, filed Nov. 6, 2019.

List of IBM Patents or Patent Applications Treated as Related; (Appendix P), Filed Mar. 6, 2020, 2 pages.

List of IBM Patents or Patent Applications Treated as Related; (Appendix P), Filed Oct. 14, 2019, 2 pages.

List of IBM Patents or Patent Applications Treated as Related; (Appendix P), Filed Oct. 2, 2019, 2 pages.

Notification of Transmittal of The International Search Report and The Written Opinion of the International Searching Authority, International Application No. PCT/IB2018/052075, dated Jul. 26, 2018, 12 pgs.

\* cited by examiner

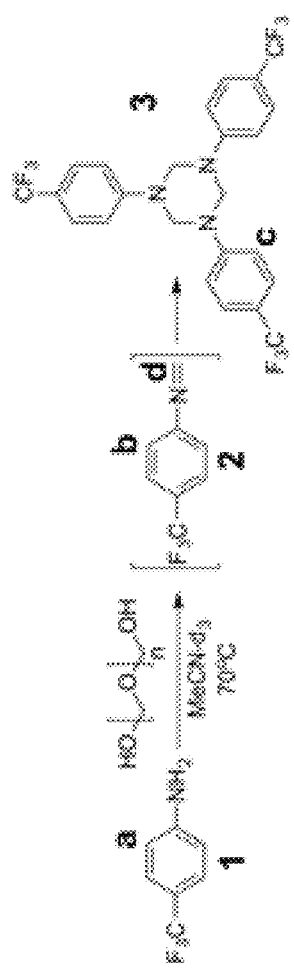
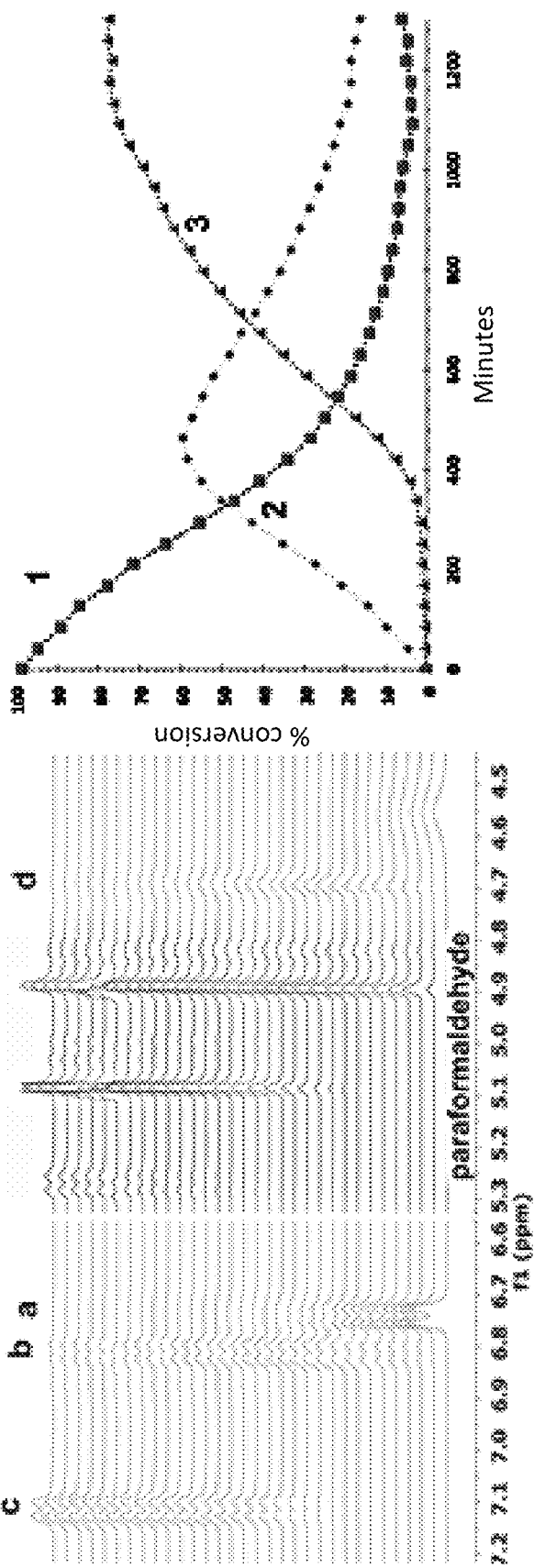
FIG. 2A
FIG. 2B

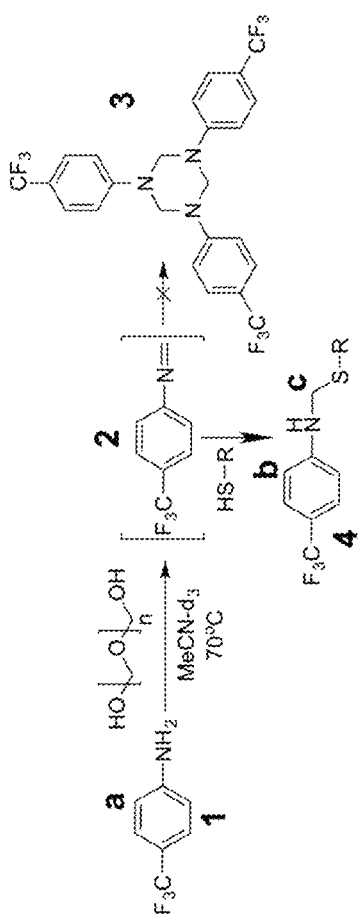
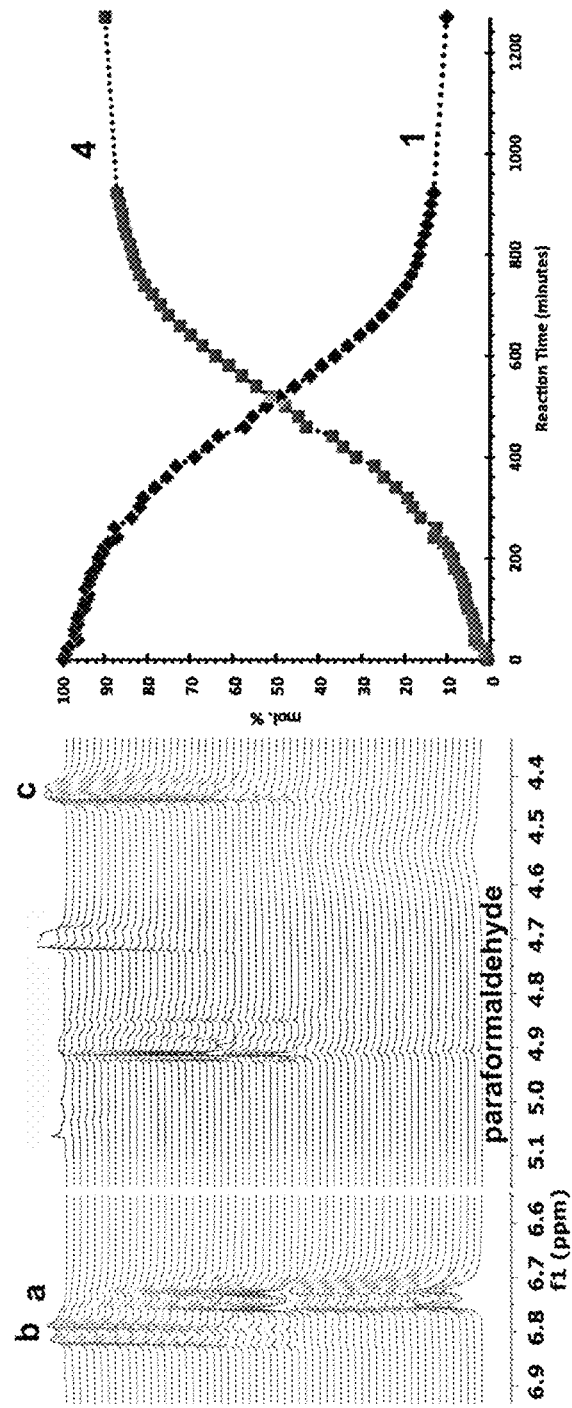
FIG. 3A
FIG. 3B

FLUORINATED NETWORKS FOR ANTI-FOULING SURFACES

BACKGROUND

The present invention relates in general to fluorinated polymers. More specifically, the present invention relates to fluorinated networks for anti-fouling surfaces.

The accumulation of microorganisms on wetted surfaces, or biofouling, is a common challenge for materials in a broad range of applications, such as medical devices, marine instruments, food processing, and even domestic drains. Generally, bacteria initiate biofouling by forming of biofilms, which are highly ordered adherent colonies, frequently within a self-produced matrix of extracellular polymeric substance. Biofilms can accumulate, for example, on surfaces of medical devices, including implantable medical devices, as well as surfaces in hospital or medical settings.

Biofilms potentially release harmful toxins, and microorganisms easily spread once biofilms are formed, which can lead to malfunction of implantable devices. Once a biofilm is formed on an implantable medical device, extreme measures, such as removal of the infected implanted device from the patient's body are often the only viable management options. Although disinfection techniques and prophylactic antibiotic treatment are used to prevent colonization during procedures, such practice is not always effective in preventing perioperative bacterial colonization.

Antibiotic treatments to eliminate colonization and infection associated with implantable substances and devices can be limited in their ability to eradicate bacteria and fungi involved in biofilm formation processes. For example, the concentration of antibiotics deep inside the biofilm can be too low to be effective, which is in part due to limited diffusion. Generally, antibiotics also may be unable to eliminate all pathogen cells, which are usually accomplished by the immune system that may not function optimally in the presence of implantable devices. Furthermore, microorganisms possess the ability to persist, i.e., to become metabolically inactive and thus relatively resistant to antibiotics. Antibiotic resistance thus makes treating device-associated infections even more challenging. In fact, antibiotic resistance is frequently encountered with microorganisms that cause device-associated infections (e.g., *Enterococci* and *Staphylococci*).

Consequently, considerable efforts were dedicated in recent years to developing antibacterial surfaces, in particular, in developing antifouling surfaces that prevent the adhesion of microorganisms. Current technologies, however, can suffer from poor long-term antibacterial performance and stability, the undesirable development of bacterial resistance, or limited scalability to an industrial setting.

Accordingly, there is a need to prevent surfaces of medical devices from forming biofilms and fouling. Forming polymeric coatings on surfaces of medical devices is one option to prevent biofouling.

Polythioaminals are a potential polymer that could be useful for forming such a coating. Polythioaminal polymers have potential applications in numerous arenas, for example, in facile preparation of therapeutic/drug conjugates, self-healing materials, and degradable hydrogels. Scheme 1 below depicts a reaction for synthesizing polythioaminals using hexahydrotriazine (HT). A dithiol (1) reacts with HT (2), releasing a substituted primary amine (3) to form the substituted polythioaminal (4).

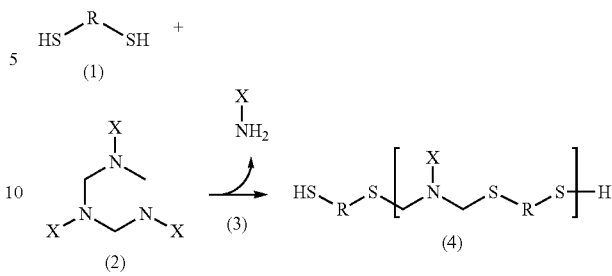

Scheme 1

HTs, as shown in Scheme 1, and their thermosetting polymer analogues, PHTs, have attracted recent attention in the materials space because they exhibit a number of attractive properties, such as healability, recyclability, and even as detectors for heavy metals. HTs also demonstrate unique reactivity towards sulfur containing compounds. Hydrogen sulfide, for instance, readily reacts with HTs at room temperature to form dithioazine, where the six-member HT ring undergoes replacement of two nitrogen atoms with sulfur. Organic thiols will also react with HTs to produce thioaminals, as shown in Scheme 1, a transformation that has been exploited to generate linear step-growth polythioaminals.

However, current synthetic routes, for example as shown in Scheme 1, for forming polythioaminals have some challenges that have made them sub-optimal for such applications. A limiting factor in the polymerization shown in Scheme 1 above is the identity of the substituent of the HT (2) ("X"). In particular, as the size of "X" increases, the molecular weight of the polymer decreases. Therefore, high molecular weight polymers are only generated with short aliphatic HT substituents, which restrict the chemical diversity of the resulting polymers.

The relationship between the size of the HT (2) substituents, "X," and the product polythioaminal (4) molecular weight is the result of the substituted primary amine (3) generated after the reaction of the dithiol (1) with the HT (2). The formation of this amine (3) influences the reaction equilibrium, preventing further reaction of thiols (1) with HTs (2) and necessitating subsequent removal (in vacuo) to access high molecular weight polythioaminals (4). Therefore, as the mass of the substituent ("X") increases, the volatility of the liberated substituted primary amine (3) is reduced, thereby making the polymerization increasingly difficult to drive to high molecular weights.

Therefore, alternative chemistries that can provide access to polythioaminals that are not restricted by the volatility of a side product are needed. Such chemistries can provide access to more chemically diverse polymers, which can allow polythioaminal polymers to be used as coatings on surfaces, such as medical devices.

SUMMARY

Embodiments of the present invention are directed to a method of making an antifouling coating. The method includes forming a polythioaminal polymer by reacting a fluorinated primary amine with an aldehyde to form an intermediate imine, and then reacting the intermediate imine with a dithiol. The method further includes depositing the polythioaminal on a substrate, and increasing a temperature of the polythioaminal deposited on the substrate to crosslink the polythioaminal and increase a contact angle of the substrate with crosslinked polythioaminal. Forming the intermediate imine and then reacting the intermediate imine with a dithiol provides the advantage of being able to form a polythioaminal without the use of HT monomers that form amine side products, which allows incorporation of larger molecular weight substituents for the fluorinated primary amine.

According to one or more embodiments, a method of making a hydrophobic antifouling coating includes forming a linear polythioaminal polymer by reacting a fluorinated dianiline derivative with a paraformaldehyde to form an intermediate imine, and then reacting the intermediate imine with a dithiol. The method includes disposing the linear polythioaminal polymer on a surface of a substrate, and increasing a temperature of the linear polythioaminal polymer to crosslink the linear polythioaminal polymer and increase a contact angle of the substrate with crosslinked polythioaminal. Forming the intermediate imine and then reacting the intermediate imine with a dithiol provides the advantage of being able to form a polythioaminal without the use of HT monomers that form amine side products, which allows incorporation of larger molecular weight substituents for the fluorinated aniline.

According to one or more embodiments, a method of making a hydrophobic coating on a surface of a medical device includes forming a polythioaminal polymer by reacting a fluorinated aniline with an aldehyde to form an intermediate imine, and then reacting the intermediate imine with a dithiol. The method includes depositing the polythioaminal polymer on a surface of the medical device. The method further includes increasing a temperature of the polythioaminal polymer to increase a contact angle of the polythioaminal polymer with the surface of the medical device. Forming the intermediate imine and then reacting the intermediate imine with a dithiol provides the advantage of being able to form a polythioaminal polymer without the use of HT monomers that form amine side products, which allows incorporation of larger molecular weight substituents for the fluorinated aniline.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

FIG. 2A depicts a reaction scheme and nuclear magnetic resonance (NMR) spectrum according to one or more embodiments of the invention;

FIG. 2B depicts a graph showing % conversion of a starting material over time according to one or more embodiments of the invention;

FIG. 3A depicts a reaction scheme and NMR spectrum according to one or more embodiments of the invention;

FIG. 3B depicts a graph showing mole % of a starting material and converted product formation over time according to one or more embodiments of the invention;

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two or three digit reference numbers. With minor exceptions, the leftmost digit(s) of each reference number correspond to the figure in which its element is first illustrated.

DETAILED DESCRIPTION

Turning now to an overview of technologies that are more specifically relevant to aspects of the invention, alternative chemistries to form polythioaminals that are not restricted by the volatility of a side product are needed. Such chemistries can provide access to more chemically diverse polymers, which can allow polythioaminal polymers to be used as coatings on surfaces, such as medical devices.

Turning now to an overview of the aspects of the invention, one or more embodiments of the invention address the above-described shortcomings by providing methods of making networks and coatings with highly fluorinated polythioaminals. The networks and coatings are disposed onto surfaces that are susceptible to biofouling, for example, on surfaces of medical devices. The described reaction schemes are an alternative synthetic strategy to form polythioaminals without the use of HT monomers. Stable imine intermediates are formed that react with thiols with a high conversion rate. The reactions described herein form highly fluorinated networks and hydrophobic coatings on susceptible surfaces, for example, of medical devices, marine instruments, food processing surface, or domestic drains, to provide an antifouling surface.

The above-described aspects of the invention address the shortcomings of other described approaches by allowing the incorporation of larger molecular weight substituents for the nitrogen-containing monomeric starting material. Thus, high molecular weight polythioaminals can be formed. The high molecular weight polymers also include fluorine, which can then function as antifouling coatings to prevent biofilm formation.

Figure 1:
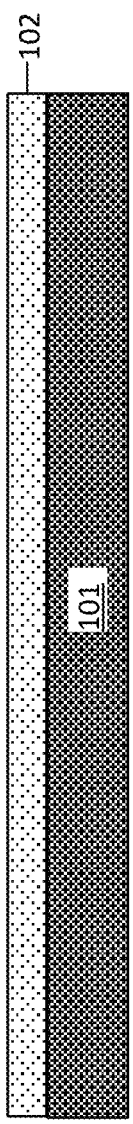
FIG. 1 depicts a cross-sectional side view of a coating formed on a substrate according to one or more embodiments of the invention.

Turning now to a detailed description of aspects of the present invention, FIG. 1 shows an antifouling coating 102 on the surface of a substrate 101. The coating includes fluorinated polythioaminal polymers, which will be described in further detail below. The coating 102 is an antifouling coating that can be formed on the surface of a medical device or a surface in a medical setting (such as a hospital) that is susceptible to contamination. The one or more fluorines present in the polythioaminal coatings provide the antifouling properties.

Non-limiting examples of implantable medical devices include, for example, prosthetic joints, heart valves, artificial hearts, vascular stents and grafts, cardiac pacemakers, defibrillators, nerve stimulation devices, gastric pacers, vascular catheters and ports (e.g., Port-A-Cath). The surfaces of these implanted materials and devices represent areas in which bacterial colonization and subsequent biofilm formation is difficult to diagnose and treat.

As described in further detail below, primary amines substituted with one or more electron withdrawing fluorine groups form reactive intermediate imines in the presence of an aldehyde. The reactive imine intermediate is quickly consumed in a self-trimerization reaction, in the absence of additional reactants. But, when the intermediate imine is reacted with a thiol, the self-trimerization reaction is suppressed. The thiol condenses with the imine intermediate to generate a polythioaminal. Thus, the reactions for forming the polythioaminal are efficient. The intermediate imine is quickly consumed by any thiol present, preventing competitive side reactions, for example any self-trimerization reactions.

Scheme 2 below is a reaction for forming a thioaminal according to one or more embodiments of the present invention. A substituted primary amine (1) that includes one or more electron withdrawing fluorines reacts with an aldehyde (2) to form a reactive intermediate (3). According to one or more embodiments, the reactive intermediate is a reactive intermediate imine. The reactive intermediate (3) reacts with a thiol (4) to drive the reaction that forms a thioaminal (5). The one or more electron withdrawing fluorine groups stabilize in situ imine formation.

Scheme 2

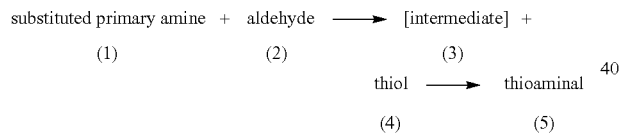

Scheme 3 is a reaction for initially forming the reactive intermediate according to one or more embodiments of the present invention. As mentioned above, reactive intermediate (8) is quickly consumed in a self-trimerization reaction to form substituted hexahydrotriazine (HT) (9) in the absence of additional reactants, such as the thiol in Scheme 2. According to one or more embodiments, the reactive intermediate is a reactive intermediate imine. The substituted HT (9) includes the fluorines present on the starting fluorinated amine (6). The reactive intermediate (8) is useful in the context of a polymer-forming reaction because its formation is quantitative and quickly consumed by any thiol present to prevent any competitive reaction in the formation of substituted HT (9).

Scheme 3

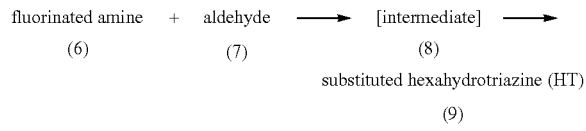

The fluorinated amine (6) includes a fluorinated aromatic ring structure and a primary amine according to one or more embodiments, for example, fluorinated aniline. In one exemplary embodiment, the fluorinated aniline is 4-trifluoromethyl aniline. The fluorinated amine includes one or more electron withdrawing fluorine groups, for example, one or more trifluoromethyl groups on an aromatic ring structure. The one or more trifluoromethyl groups can be present at any location on the aromatic ring.

The fluorinated amine (6) can include one or more additional substitutions on the aromatic ring. According to one or more embodiments, the fluorinated amine (6) includes one or more aromatic rings, which each include one or more fluorine substitutions and one or more amine substitutions.

According to exemplary embodiments, the fluorinated amine (6) has the following structure:

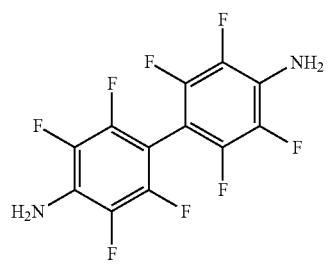 [SMILES: Nc1c(F)c(F)c(-c2c(F)c(F)c(N)c(F)c2F)c(F)c1F]

According to one or more exemplary embodiments, the fluorinated amine (6) has the following structure:

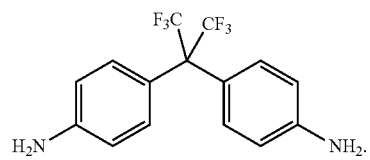 [SMILES: Nc1ccc(C(c2ccc(N)cc2)(C(F)(F)F)C(F)(F)F)cc1]

The aldehyde (7) is formaldehyde (methanal) or paraformaldehyde according to one or more embodiments. Other non-limiting examples of aldehydes that can be used include ethanal, propanal, butanal, or a combination thereof. The aldehyde is any aldehyde that can react with the fluorinated amine (6) to form an intermediate imine (8).

The reactive intermediate (8) formed depends on the identities of the fluorinated amine (6) and the aldehyde (7). Imine formation from a fluorinated primary amine and aldehyde occurs as follows: $R_1-NH_2+R_2CHO \rightarrow R_1-N=C-R_2+H_2O$. Water is eliminated in the reaction. $R_1$ includes one or more fluorine atoms or groups, such as trifluoromethyl groups. $R_2$ is H.

The substituted HT (9) results as the reactive intermediate (8) self-trimerizes. As mentioned above, this reaction is displaced in the presence of thiols.

Scheme 4 is a reaction for converting the reactive intermediate (8) into a thioaminal (11) according to one or more embodiments of the invention. According to one or more embodiments, the reactive intermediate is a reactive intermediate imine. When the reactive intermediate (8) is introduced to a thiol (10), a thioaminal (11) is formed, and the formation of the HT (9) in Scheme 3 is suppressed. The thioaminal (11) is formed in high yield and independent of the identities of the substitutions on the fluorinated amine (6) starting material.

Scheme 4

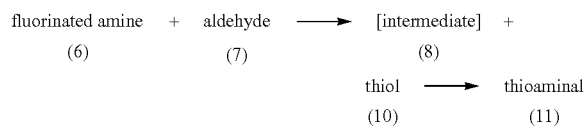

The fluorinated amine (6) is a fluorinated primary amine, and the aldehyde is paraformaldehyde according to one or more embodiments. The formation of the thioaminal (11) occurs as follows: $R_1\text{—}NH_2 + R_2CHO \rightarrow [R_1\text{—}N\text{=}CHR_2] + HS\text{—}R_3 \rightarrow R_1\text{—}NH\text{—}CHR_2\text{—}SR_3$. $R_1$ includes one or more fluorine atoms or groups, such as trifluoromethyl groups. $R_2$ is H or a hydrocarbon chain with any number of carbons. In some embodiments, $R_2$ includes from 1 to 10 carbons. $R_3$ is a hydrocarbon chain with any number of carbons. In some embodiments, $R_3$ includes from 1 to 20 carbons.

A polymeric thioaminal (polthioaminal) is also formed by a polycondensation reaction. An imine is formed as an intermediate. Scheme 5 shows a fluorine substituted aniline (12) reacting with aldehyde (7) to form reactive intermediate (13). The reactive intermediate (13) reacts with dithiol (14) to form the polythioaminal (15).

Scheme 5

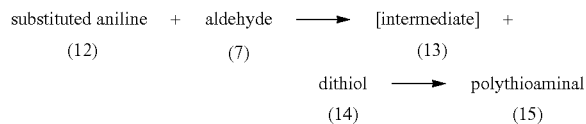

The substituted aniline (12) includes at least one aromatic ring and at least one primary amine. The substitutions on the aniline (12) include one or more fluorine atoms or fluorine-containing groups, for example, trifluoromethyl groups. The substituted aniline (12) is a diamine according to one or more embodiments. The substituted aniline (12) is a fluorinated dianiline according to one or more embodiments. According to an exemplary embodiment, the substituted aniline (12) is (hexafluoroisopropylidene)dianiline.

The aldehyde (7) includes one or more carbons. According to one or more embodiments, the aldehyde (7) is formaldehyde or paraformaldehyde.

The reactive intermediate (13) is an intermediate that reacts with the dithiol (14) to form the polythioaminal (15). According to an exemplary embodiment, the dithiol (14) is 1,6-hexanedithiol. According to other embodiments, the dithiol (14) is poly(ethylene) glycol dithiol or dithioerythritol. In other embodiments, the dithiol (14) includes a hydrocarbon chain with any length carbon chain, any polyalcohol, or any length polyethylene glycol dithiol.

The polymeric polythioaminal (15) proceeds to high conversion, by in-situ forming a reactive intermediate imine (13) that condenses with the dithiol (14) to generate the polythioaminal (15).

The reaction occurs as follows: $NH_2\text{—}R_1\text{—}NH_2 + R_2CHO \rightarrow [R_2\text{—}CH\text{=}N\text{—}R_1\text{—}N\text{=}CH\text{—}R_2] + HS\text{—}R_3\text{—}SH \rightarrow \text{—}[S\text{—}R_3\text{—}S\text{—}CH(R_2)\text{—}NH\text{—}R_1\text{—}NH\text{—}CH(R_2)]_n\text{—}S\text{—}R_3\text{—}SH$. $R_1$ includes one or more aromatic rings and one or more fluorine containing groups. $R_2$ and $R_3$ include hydrocarbon chains, with the number of carbons not being limited. The polythioaminal (15) has an "n" of about 1 to about 15.

The reaction proceeds to produce a polythioaminal (15) of high molecular weight. According to one or more embodiments, the polythioaminal has a molecular weight of less than 8,000 g mol$^{1}$. In some other embodiments, the polythioaminal has a molecular weight in a range from about 5,000 to about 25,000 g mol$^{-1}$.

In contrast to Scheme 1, for example, amines affecting the reaction equilibrium are not being liberated. The liberated amine in Scheme 1 must be removed to drive the reaction towards formation of the thioaminal. Further, as mentioned with reference to Scheme 1, the identities of the substituents on the amine affect the amine's volatility, with larger substituents decreasing the volatility, and therefore, reducing the conversion rate to the high molecular weight polythioaminals.

Non-limiting examples of substituents can be present on the substituted primary amine (1) in Scheme 2, fluorinated amine (6) in Schemes 3 and 4, and substituted aniline (12) in Scheme 5 include fluorine groups, amine groups, $CF_3$ groups, or a combination thereof.

High molecular weight substituents can be present on the fluorinated amine starting materials. According to one or more embodiments, the substituted primary amine (1) in Scheme 2, fluorinated amine (6) in Schemes 3 and 4, and substituted aniline (12) in Scheme 5 can have molecular weights of at least 31 g mol$^{-1}$, or in a range from about 100 to about 20,000 g mol$^{-1}$.

Because the reactions described herein do not liberate an amine, the conversion to the polythioaminal occurs at a high rate, regardless of the substitutions on the starting material. According to one or more embodiments, at least 99.99% of the initial fluorinated primary amine is converted to the polythioaminal. According to one or more embodiments, about 100% of the initial fluorinated primary amine is converted to the polythioaminal.

The temperature at which the reactions proceed to form the polythioaminals affects the extent of crosslinking that occurs to form a network that can be used as a hydrophobic antifouling coating on a substrate. At lower temperatures, for example, from about 25 to about 100° C., linear polymers are formed. As the temperature is increased to about 110 to about 200° C., the linear polymers undergo multiple substitutions at the nitrogen to form a cross-linked network. According to one or more embodiments, the temperature is increased to at least 100° C. to crosslink the linear polythioaminal and form a network on a surface of a substrate.

Figure 5:
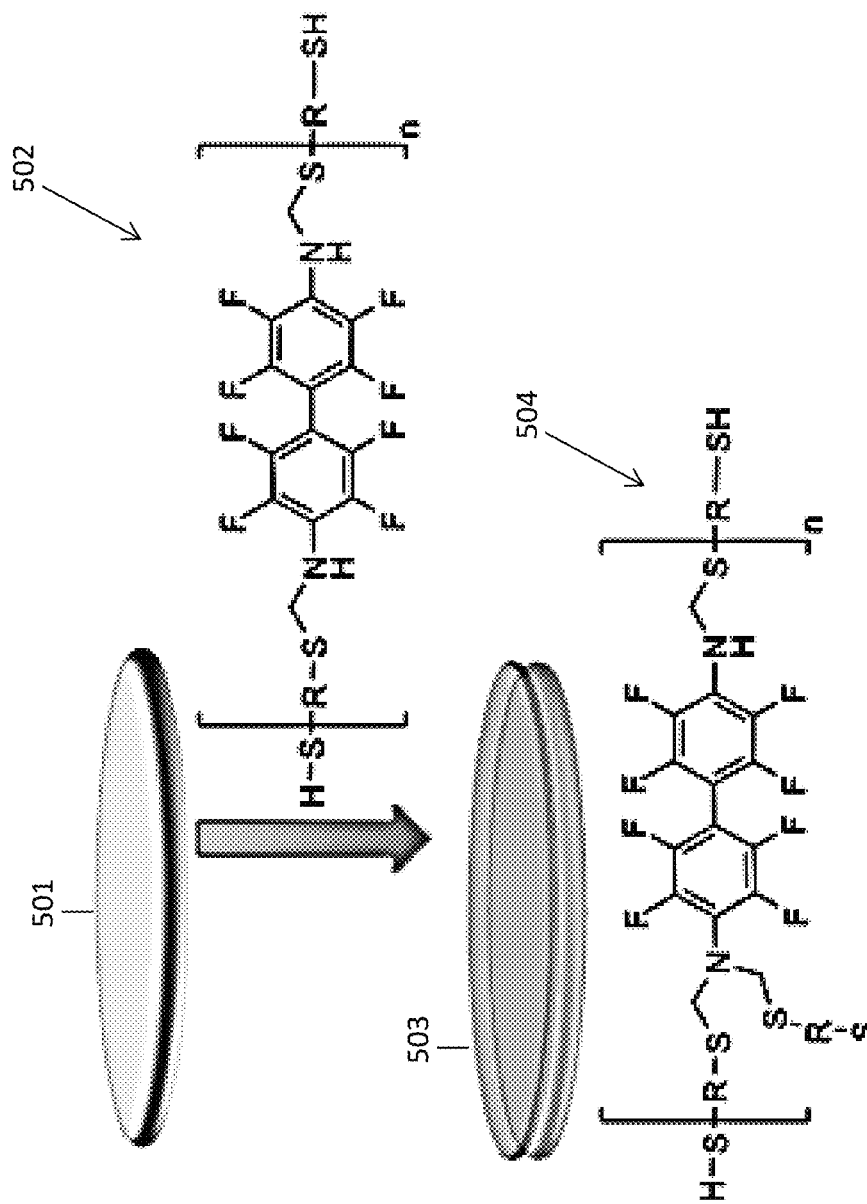
FIG. 5 depicts a method for forming a coating on a substrate according to one or more embodiments of the invention.

Thus, as shown in FIG. 5, a linear polyaminal 502 can be disposed onto the surface of a substrate 501. The polydispersity index (PDI) of the linear polythioaminal 502 is about 2 according to one or more embodiments. The substrate 502 and linear polythioaminal 502 is heated to form a coating 503 (or film) of a crosslinked network 504 of the polyaminal. According to one or more embodiments, the coating 503 is a film that takes the shape of the substrate 501. As the fluorine content of the starting material increases, the contact angle of the resulting coating 503 increases. The contact angle increases to at least 100° according to some embodiments. The PDI of the crosslinked network 504 also increases as the temperature is increased.

According to one or more embodiments, a linear polyaminal formed as described herein is disposed, for example by spin-coating, onto the surface of a substrate. The substrate is then heated to form a cross-linked network on the surface of the substrate.

According to one or more embodiments, a method of making an antifouling coating includes forming a polythioaminal polymer by reacting a fluorinated primary amine with an aldehyde to form an intermediate imine, and then reacting the intermediate imine with a dithiol. The method further includes disposing the polythioaminal on a substrate. The method further includes increasing a temperature of the polythioaminal disposed on the substrate to crosslink the polythioaminal and increase a contact angle of the substrate with crosslinked polythioaminal.

Forming the intermediate imine and then reacting the intermediate imine with a dithiol provides the advantage of being able to form a polythioaminal without the use of HT monomers that form amine side products, which allows incorporation of larger molecular weight substituents for the fluorinated primary amine.

Embodiments where the fluorinated primary amine is a diamine have advantages of polymerizing the polythioaminal to even higher molecular weight.

According to one or more embodiments, a method of making a hydrophobic antifouling coating includes forming a linear polythioaminal polymer by reacting a fluorinated dianiline derivative with a paraformaldehyde to form an intermediate imine, and then reacting the intermediate imine with a dithiol. The method includes disposing the linear polythioaminal polymer on a surface of a substrate. The method further includes increasing a temperature of the linear polythioaminal polymer to crosslink the linear polythioaminal polymer and increase a contact angle of the substrate with crosslinked polythioaminal.

Forming the intermediate imine and then reacting the intermediate imine with a dithiol provides the advantage of being able to form a polythioaminal without the use of HT monomers that form amine side products, which allows incorporation of larger molecular weight substituents for the fluorinated primary amine.

Embodiments where the contact angle is at least 100° have advantages of forming a thick hydrophobic coating that prevents biofilm.

According to one or more embodiments, a method of making a hydrophobic coating on a surface of a medical device includes forming a polythioaminal polymer by reacting a fluorinated aniline with an aldehyde to form an intermediate imine, and then reacting the intermediate imine with a dithiol. The method includes disposing the polythioaminal polymer on a surface of the medical device. The method further includes increasing a temperature of the polythioaminal polymer to increase a contact angle of the polythioaminal polymer with the surface of the medical device.

Embodiments where increasing the temperature of the polythioaminal polymer induces crosslinking by forming substitutions at nitrogen groups have advantages of forming a highly crosslinked network that is formed after a linear polymer is deposited on the surface of the medical device.

EXAMPLES

Example 1

To explore the potential of imines to form thioaminals, model reactions were performed with aniline derivatives substituted with electron-withdrawing trifluoromethyl substituents. FIG. 2A depicts the reaction scheme and corresponding nuclear magnetic resonance (NMR) spectra for the reaction of 4-trifuoromethyl aniline (1) with paraformaldehyde (1.5 eq.) in acetonitrile at 70° C. 4-trifluoromethyl aniline (1) formed an intermediate imine (2) that quickly underwent cyclization to form trimer (3), as shown by NMR monitoring.

The reaction was monitored over the course of 20 hours, with spectra taken after every 40 minutes. From $^1$H-NMR peaks shown in FIG. 2A, the peaks (a) associated with the starting material (1) decreased in intensity as several new peaks (b) and (d), associated with the imine (2), begin to grow. However, after a period of about 500 minutes (8.3 hours), the new peaks decreased in intensity as peak (c), associated with trimer (3) began to grow. During the course of the reaction, peaks associated with the decomposition of paraformaldehyde grew in intensity.

Using shorter reaction times, peaks associated with imine (2) were confirmed using a combination of $^{13}$C-NMR and 2D-NMR (not shown). $^{13}$C-NMR was useful in providing diagnostic indications of the formation of both imine (2) and trimer (3) where downfield resonances could be observed characteristic of the carbon associated with protons in peak (d). These results showed that the formation of imine (2) was a reactive intermediate that was quickly consumed in the self-trimerization to form trimer (3) in about 70% conversion, as shown in FIG. 2B. The generation of imine (2) was thus useful as a polymer forming reaction because its generation was quantitative.

Example 2

The efficiency for the in-situ generation of imines and subsequent reaction with the presence of thiols to form thioaminals was also explored using a model NMR scale reaction using 4-trifuoromethyl aniline (1) in the presence of 1-butane thiol (4) (1 eq.) and paraformaldehyde (1.5 eq.) at 70° C. in CD$_3$CN. FIG. 3A depicts the reaction scheme and corresponding NMR spectra for the reaction of 4-trifuoromethyl aniline (1) with paraformaldehyde (1.5 eq.) in acetonitrile at 70° C. and 1-butane thiol (4).

Interestingly, in the presence of a thiol, the formation of trimer (3) was completely suppressed. No diagnostic peaks were observed corresponding with the trimer (3) when observing either $^1$H or $^{13}$C nuclei. Conversion to the thioaminal could be followed by the growth of peaks (b) and (c), associated with polythioaminal (4), while those corresponding with 4-trifluoroaniline (1) decreased in intensity. After about 20 hours, the generation of thioaminal (4) plateaued at nearly quantitative conversion (about 90%), as shown in FIG. 3B.

Example 3

Figures 4A, 4B:
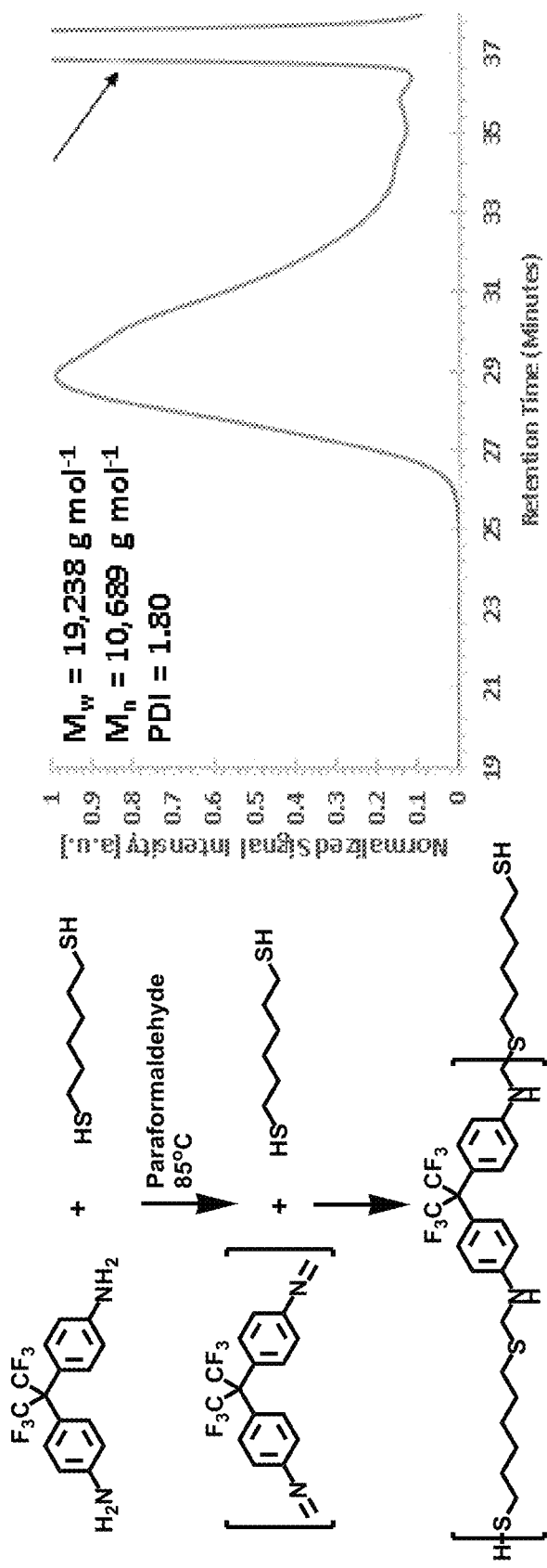
FIG. 4A depicts a reaction scheme according to one or more embodiments of the invention.
FIG. 4B depicts a gel permeation chromatography (GPC) spectrum showing formation of a product according to one or more embodiments of the invention.

To exploit the imine-thiol reaction in a polycondensation reaction, 4,4'-(hexafluoroisopropylidene)dianiline was reacted in bulk with 1,6-hexanedithiol in equimolar ratios with an excess of paraformaldehyde (2.5 eq.) at 85° C., as shown in FIG. 4A. Over the course of 18 hours, the reaction proceeded to high conversion. A polymeric material was generated from the in-situ generation of a reactive intermediate imine that condensed with 1,6-hexanedithiol to generate a polythioaminal (see FIG. 4A). The product polythioaminal was confirmed by gel permeation chromatography (GPC), as shown in FIG. 4B. The $M_w$ of the polythioaminal was 19,238 g mol$^{-1}$ ($M_n$=10,689 g mol$^{-1}$).

Example 4

To highlight the effect of the electron withdrawing fluorines on the generation of the polymer, a control reaction was performed using a monomer without trifluoromethyl substituents, 4,4'-diaminodiphenylmethane, using the same reaction conditions described in Example 3 and the same dithiol. Only a low molecular weight polymer was generated ($M_w$=4,810 g mol-1, $M_n$=2,658 g mol-1). Without being bound by theory, the lower molecular weight was believed to result from an uncontrolled series of reactions that included the formation of cyclic products, imine, and reaction with either of these with the dithiol. Because amines severely reduce the formation of thioaminals, any amines generated, liberated, or those remaining unreacted can prevent the polycondensation reaction from reaching a higher molecular weight.

Example 5

The role of temperature on the formation of polythioaminals was assessed. It was found that at lower temperatures, only linear polythioaminals are formed, in which the polydispersity index (PDI) is ~2.00. However, as the temperature increased to 110° C., the linear polymer began to undergo multiple substitutions at the nitrogen, which increased the PDI and formed a network (see FIG. 5 for example).

Example 6

A polythioaminal was prepared. A fluorinated amine (A) having the following structure was combined with paraformaldehyde as follows.

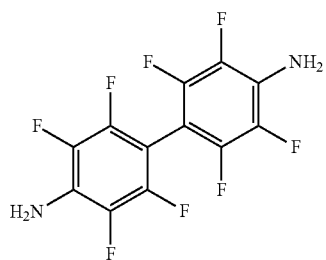 [SMILES: Nc1c(F)c(F)c(-c2c(F)c(F)c(N)c(F)c2F)c(F)c1F]

770 mg of A (2.35 mmol)+140.8 mg paraformaldehyde+ 358 μL hexane dithiol in 2 mL of N-methyl pyrrolidone were added to a scintillation vial with a Teflon coated stir-bar. The vial was purged with nitrogen and then sealed and heated to 70° C. in an inert nitrogen atmosphere. The reaction was run over the course of about 60 hours to build up the molecular weight of the linear polymer. Oligomers were observed by gel permeation chromatography (GPC). The linear oligomer could be coated on a silicon wafer by drop-cast method then was cured in a vacuum oven overnight at 140° C.

Example 7

A polythioaminal was prepared. A fluorinated amine (B) having the following structure was combined with paraformaldehyde as follows.

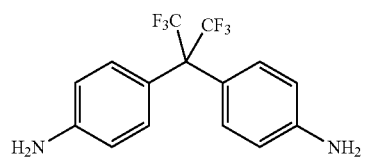 [SMILES: Nc1ccc(C(c2ccc(N)cc2)(C(F)(F)F)C(F)(F)F)cc1]

0.765 g (2.29 mmol) B+137.3 mg paraformaldehyde+350 μL hexane dithiol were added to a scintillation vial followed by 1.5 mL N-methylpyrrolidone. The vial flushed with nitrogen. The vial was then sealed and heated to 75° C. After about 24 hours, the molecular weight was observed by GPC, which was about 4,200 g mol$^{-1}$. After about 94 hours of heating, the molecular weight increased slightly to 6,600 g mol$^{-1}$, and after about 110 hours, the molecular weight again increased to 6,800 g mol$^{-1}$. The PDI also increased and after 24 hours reached 2.03. After 94 hours, the PDI increased to 2.5, and after 110 hours, the PDI was 2.6. When the temperature was increased to 110° C., the solution began to gel, which indicated a network polymer was forming. The soluble fraction of polymer exhibited a molecular weight of 100,500 g mol$^1$ with a broad PDI of 16.4.

Various embodiments of the present invention are described herein with reference to the related drawings. Alternative embodiments can be devised without departing from the scope of this invention. Although various connections and positional relationships (e.g., over, below, adjacent, etc.) are set forth between elements in the following description and in the drawings, persons skilled in the art will recognize that many of the positional relationships described herein are orientation-independent when the described functionality is maintained even though the orientation is changed. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper," "lower," "right," "left," "vertical," "horizontal," "top," "bottom," and derivatives thereof shall relate to the described structures and methods, as oriented in the drawing figures. The terms "overlying," "atop," "on top," "positioned on" or "positioned atop" mean that a first element, such as a first structure, is present on a second element, such as a second structure, wherein intervening elements such as an interface structure can be present between the first element and the second element.

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A method of making an antifouling coating, the method comprising:
   forming a poly(thioaminal) polymer by reacting a fluorinated primary amine with an aldehyde to form an intermediate imine, and then reacting the intermediate imine with a dithiol;
   depositing the poly(thioaminal) on a substrate; and
   increasing a temperature of the poly(thioaminal) deposited on the substrate to crosslink the poly(thioaminal) and increase a contact angle of the substrate with crosslinked poly(thioaminal).

2. The method of claim 1, where the fluorinated primary amine is a diamine.

3. The method of claim 1, where the fluorinated primary amine comprises at least one aromatic ring.

4. The method of claim 1, where the fluorinated primary amine is a dianiline.

5. The method of claim 1, wherein depositing the poly(thioaminal) on the substrate is by spin-coating.

6. The method of claim 1, where the aldehyde is paraformaldehyde.

7. The method of claim 1, where the dithiol is 1,6-hexanedithiol.

8. The method of claim 1, where the polythioaminal is a linear polymer.

9. A method of making a hydrophobic antifouling coating, the method comprising:
   forming a linear poly(thioaminal) polymer by reacting a fluorinated dianiline derivative with a paraformaldehyde to form an intermediate imine, and then reacting the intermediate imine with a dithiol;
   disposing the linear poly(thioaminal) polymer on a surface of a substrate; and
   increasing a temperature of the linear poly(thioaminal) polymer to crosslink the linear poly(thioaminal) polymer and increase a contact angle of the substrate with crosslinked poly(thioaminal).

10. The method of claim 9, where the substrate is a surface of a medical device.

11. The method of claim 10, where the medical device is an implantable medical device.

12. The method of claim 9, where the contact angle is at least 100°.

13. The method of claim 9, where the temperature is increased to at least 100° C.

14. The method of claim 9, where the dithiol is 1,6-hexanedithiol.

15. A method of making a hydrophobic coating on a surface of a medical device, the method comprising:
   forming a poly(thioaminal) polymer by reacting a fluorinated aniline with an aldehyde to form an intermediate imine, and then reacting the intermediate imine with a dithiol;
   depositing the poly(thioaminal) polymer on a surface of the medical device; and
   increasing a temperature of the poly(thioaminal) polymer to increase a contact angle of the poly(thioaminal) polymer with the surface of the medical device.

16. The method of claim 15, wherein the aldehyde is paraformaldehyde.

17. The method of claim 15, wherein forming the poly(thioaminal) polymer forms a linear polymer.

18. The method of claim 17, wherein increasing the temperature of the poly(thioaminal) polymer induces crosslinking by forming substitutions at nitrogen groups.

19. The method of claim 15, wherein a polydispersity index (PDI) of the poly(thioaminal) polymer is about 2.

20. The method of claim 19, wherein increasing the temperature increases the PDI of the poly(thioaminal) polymer.

* * * * *